United States Patent [19]

Sudar et al.

[11] 4,275,352
[45] Jun. 23, 1981

[54] SEA WATER CONDUCTIVITY CELL

[75] Inventors: Robert B. Sudar; Edward L. Lewis; Albert W. Koppel, all of Victoria, Canada

[73] Assignee: Canadian Patents & Dev. Ltd., Ottawa, Canada

[21] Appl. No.: 17,731

[22] Filed: Mar. 5, 1979

[51] Int. Cl.$^3$ .......................................... G01N 27/42
[52] U.S. Cl. .................................. 324/449; 324/442
[58] Field of Search ............................... 324/442, 449

[56] References Cited

U.S. PATENT DOCUMENTS

| | | | |
|---|---|---|---|
| 3,582,768 | 6/1971 | Watson | 324/449 |
| 3,906,353 | 9/1975 | Murdock | 324/442 |
| 3,993,945 | 11/1976 | Warmoth | 324/449 |

Primary Examiner—Michael J. Tokar
Attorney, Agent, or Firm—Edward Rymek

[57] ABSTRACT

The conductivity cell consists of a first set of electrodes fixed rigidly to a second set of electrodes. Each set of electrodes has an insulating material support with an electrode well through it, and three spaced electrodes positioned sequentially within the well. In one embodiment, the support is a glass tube and the three electrodes are deposited on the inner surface of the glass tubes. In a further embodiment, the three electrodes are washer shaped conductive strips fixed within the electrode well and spaced by two washer shaped non-conductive strips also fixed within the electrode well. Each set of electrodes further includes a glass tubing fixed within the electrode well between each outer electrode and the outer end of the electrode well. In another embodiment, washer shaped electrodes are recessed in the wall of the electrode well such that the surface of the strips are flush with the electrode well surface. The two outer electrodes are electrically connected together as well as electrically insulated from the center electrode. The two outer electrodes carry current through the sea water between the wells while the center electrode in each well is a voltage electrode. The two wells may be substantially parallel and the cell may further have a temperature sensing device.

9 Claims, 9 Drawing Figures

SEA WATER CONDUCTIVITY CELL

BACKGROUND OF THE INVENTION

This invention is directed to the salinity measurement of sea water, and in particular to a conductivity cell for the determination of sea water salinity.

For a long time there has been a requirement for a moorable sensor chain to record conductivity and temperature values in coastal regions from which salinity may be determined. A major limitation in past attempts to fill this need has been lack of stability in the conductivity sensor cell constant caused by biological activity, dimensional changes, or corrosion. Another problem in chain construction was that most conductivity sensors employed an inductive principle which made it difficult to place them more than a few feet from their associated electronics. Thus a chain would be assembled from a number of individual sensors complete with electronics rather than permitting them to be multiplexed onto a single electronics board, a much cheaper construction. In contrast the four electrode method of measuring conductivity typically operates at frequencies where the inductive effects associated with long lines separating sensor and electronics no longer are significant.

By modifying the electrodes, it is possible to minimize the consequences of corrosion or dimensional changes in the immediate vicinity of the electrodes themselves. In the four electrode system described in the publication by T. M. Dauphinee—"Some Applications of DC and Square Wave AC Techniques to Undersea Measurements"—Paper No. 68-635, Instrument Society of America Annual Conference, 1968, two "voltage" electrodes sense a potential difference between fixed points along a current path between two "current" electrodes, the current being varied to keep this voltage constant. The current then provides a measure of the cell conductance. Changes in current flow path due to corrosion, etc., will effect the sensed voltage particularly if the electrodes carry any current due either to the finite input impedance of the amplifier or because they partially shunt the seawater circuit. A very high input impedance is offered by Dauphinee's circuit and the voltage electrodes are recessed to stay out of the current path. Nevertheless, variations in current density over the current electrodes as a result of changing metal/sea water interface conditions can alter the sensed voltage difference. A development of this system used for the Guildline Bench salinometer is described in the publication by T. M. Dauphinee and H. P. Klein, "A New Automated Laboratory Salinometer", Sea Technology, 16, 1975, pages 23-25. All four electrodes are placed in side arms away from the main current path so that current flow along the path interval containing the voltage electrodes is almost independent of local changes at the electrode surface. Another factor has been the need to obtain a high enough cell impedance in typical sea water to allow use of easily obtainable electronic circuit components within their normal operating range. This has usually required considerable physical constrictions in current flow which in turn have created a problem in cell flushing as different water masses move past the sensor in the chain.

SUMMARY OF THE INVENTION

It is therefore an object of this invention to provide a conductivity sensor cell having good flushing characteristics.

It is another object to provide a conductivity cell having minimum sensitivity to fouling and external effects.

It is a further object of this invention to provide a conductivity sensor cell for use in a salinity chain.

These and other objects are achieved in a conductivity cell in which a first set of electrodes are rigidly fixed to a second set of electrodes. Each set of electrodes include an insulating material support having an electrode well through it, and first, second and third electrodes spaced sequentially within the well. The first and third electrode in each set are current electrodes and may be connected together and the second electrode is a voltage electrode.

In one embodiment, each set of electrodes includes a glass tube and first, second and third electrodes deposited on the inner circumference of the glass tube. In a further embodiment, the first, second and third electrodes which are washer shaped conductive strips fixed within the electrode well, are spaced by washer shaped non-conductive strips. In addition, a glass tubing is fixed within the electrode well between each outer electrode and the end of the well. The non-conductive strips and glass tubing preferably have a radial thickness approximately equal to the thickness of the electrode conductive strips. In another embodiment, the electrodes consist of washer shaped conductive strips which are recessed in the wall of the electrode well such that the surface of the strips are flush with the electrode well surface.

The conductivity cell may either be machined or molded as a single unit, with the two electrode wells close together and substantially parallel to one another.

A temperature sensing device may also be included in the cell for measuring water temperature which is needed for salinity measurements.

DESCRIPTION OF THE PREFERRED EMBODIMENTS

Figure 1:
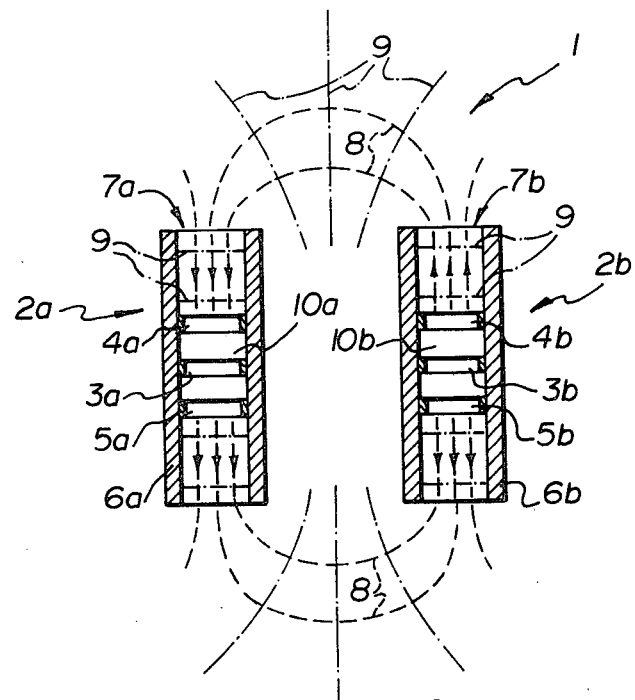
FIG. 1 is a schematic of the conductivity cell in accordance with the present invention.

The conductivity cell in accordance with the present invention, as in conventional devices, includes voltage electrodes and current electrodes, however the voltage electrodes are situated so as to be in a field free space. This is achieved by surrounding each voltage electrode by current electrodes as illustrated in FIG. 1. The cell 1 includes two spaced electrode sets 2a and 2b which are rigidly fixed with respect to one another. The sets 2a and 2b as shown are identical and symmetrically positioned with respect to one another, however this is not essential. Each electrode set 2a and 2b includes a voltage electrode 3a, 3b positioned in between two current electrodes 4a and 5a, 4b and 5b. The three electrodes in each set 2a, 2b are supported within a non-conducting material 6a, 6b which is shaped to have an electrode well 7a, 7b through it.

In operation, electrodes 4a and 5a are connected together, electrodes 4b and 5b are connected together, and an alternating current source is connected between the current electrodes 4a, 5a in set 2a and the current electrodes 4b, 5b in set 2b. When cell 1 is placed in salt water, current flows between sets 2a and 2b as represented by current field lines 8. This produces the potential field represented by lines 9. As can be seen in FIG. 1, current-free spaces 10a and 10b exist between the current electrodes 4a-5a and 4b-5b respectively, and the voltage electrodes 3a and 3b are located within these spaces. If the electronics connected to the voltage electrodes 3a, 3b has a high input impedance, no current will flow into or out of the voltage electrodes 3a, 3b due to the current free spaces 10a, 10b. By maintaining a stable voltage between the voltage electrodes 3a and 3b, in the water path surrounded by the current electrodes 4a-4b and 5a-5b, a stable current path is provided in this critical area.

In addition, the cell 1 also exhibits good flushing characteristics due to the short flushing path through the cells 7a, 7b. This helps to prevent the formation of deposits on the cell 1.

Figure 2:
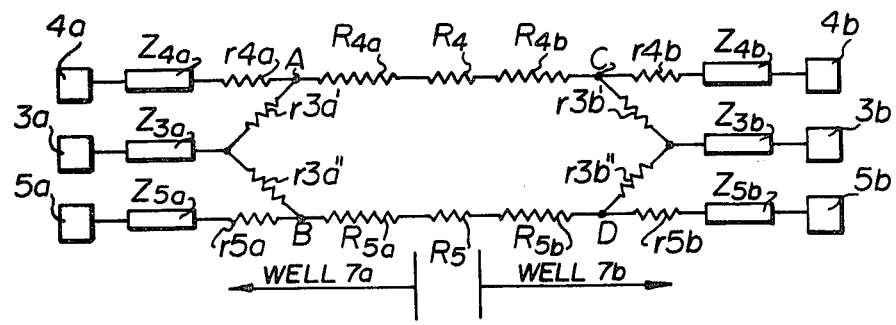
FIG. 2 is an equivalent circuit of the conductivity cell.

An equivalent circuit of the conductivity cell 1 is shown in FIG. 2. Electrodes 4a, 3a, 5a are the electrodes in set 2a and electrodes 4b, 3b, and 5b are the electrodes in set 2b as described in reference to FIG. 1. $Z_{4a}$, $Z_{3a}$, $Z_{5a}$, $Z_{4b}$, $Z_{3b}$, and $Z_{5b}$ are the polarization impedances at the respective electrodes. These impedances are a complex function of the electrode-sea water interface conditions and the magnitude of the electrode current. Since virtually no current flows in voltage electrodes 3a and 3b, $Z_{3a}$ and $Z_{3b}$ are insignificantly small.

$r_{4a}$, $r_{5a}$, $r_{4b}$, $r_{5b}$, $r_{3a}'$, $r_{3a}''$, $r_{3b}'$, and $r_{3b}''$, are sea water resistances between each electrode and the equipotential line in the sea water having the same potential as the voltage electrodes 3a, 3b in the respective well 7a, 7b. The positions of this equipotential line is located on the side of the current electrodes away from the voltage electrodes and are represented by A, B, C and D in FIG. 2. $R_{4a}$, $R_4$, and $R_{4b}$ are the sea water resistances along the current path between points A-C in FIG. 2 and $R_{5a}$, $R_5$ and $R_{5b}$ are the sea water resistances along the current path between points B-D. Resistance $R_4$ and $R_5$ are along the current path external to the wells 6a and 6b. They determine proximity effects of the cell 1 and their values are normally less than 1% of the total cell resistance. These resistances are measured by the external electronic circuitry described below and are defined by the cell constant and the resistivity of the sea water.

Figure 3:
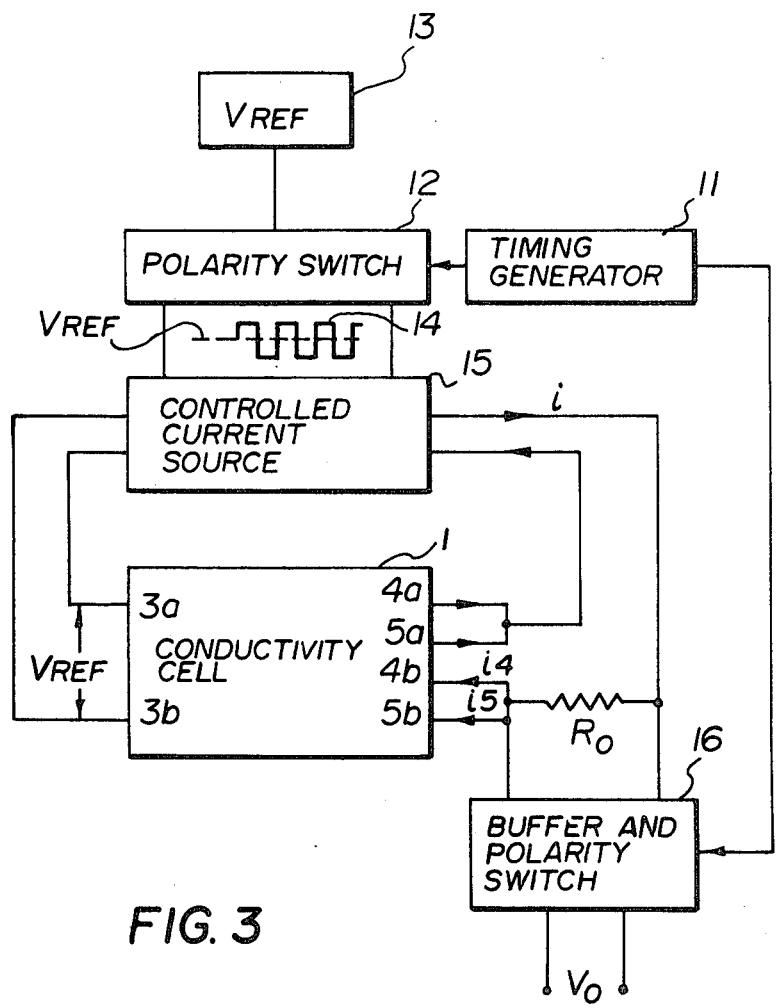
FIG. 3 illustrates a circuit for operating the conductivity cell.

The circuit illustrated in FIG. 3 operates the conductivity cell. A timing generator 11 produces timing pulses for the circuit. A polarity switch 12 is connected to a reference voltage ($V_{ref}$) source 13 which under the control of the timing generator 11, provides a square wave alternating reference voltage 14. The voltage 14 is applied to a controlled current source 15 which drives an alternating current between the current electrodes 4a-5a in electrode well 2a and the current electrodes 4b-5b in electrode well 2b through the external sea water. The voltage electrodes 3a and 3b in wells 2a and 2b are also connected to the current source 15 to control the current so that the potential across the voltage electrodes 3a-3b, is maintained equal to $V_{ref}$. The current required to do this is measured across a series resistance $R_o$ which is connected between the current electrodes 4b-5b in well 2b and the current source 15. The voltage across resistance $R_o$ is fed to a circuit 16 having a buffer and a further polarity switch controlled by the timing generator 11, to provide a dc output $V_o$. The relative timing of the polarity switches 12 and 13 are adjusted to eliminate any transient effects on the output $V_o$ due to current reversal through the cell.

From FIG. 3 it can be seen that $V_o = R_o i$ (1) where $V_o$ is the voltage across the resistance $R_o$ and i is the current flowing through the sea water. In addition, $i = i_4 + i_5$ (2), where $i_4$ is the current along one path, between electrodes 4a and 4b, and $i_5$ is the current along the other path between electrodes 5a and 5b. Since currents $i_4$ and $i_5$ are controlled to maintain a voltage $V_{ref}$ across the voltage electrodes 3a and 3b, then $$i_4 = V_{ref}/R_{4T} \tag{3}$$

and $$i_5 = V_{ref}/R_{5T} \tag{4}$$

where from FIG. 2

$$R_{4T} = R_{4a} + R_4 + R_{4b} \tag{5}$$

and $$R_{5T} = R_{5a} + R_5 + R_{5b} \tag{6}$$

Therefore, from 1, 2, 3 and 4

$$V_o = R_o \left( \frac{V_{ref}}{R_{4T}} + \frac{V_{ref}}{R_{5T}} \right) \tag{7}$$

$$V_o = \frac{R_o V_{ref}}{R_{4T} \| R_{5T}} \tag{8}$$

where $R_{4T} \| R_{5T} = \frac{R_{4T} R_{5T}}{R_{5T} + R_{4T}}$

Therefore $$V_o = \frac{R_o V_{ref}}{R_{cell}} = K_1 \frac{1}{R_{cell}} = K_1 G_{cell} = \frac{K_1}{K_{cell}} g_w \tag{9}$$

where
 $R_{cell} = R_{4T} \| R_{5T}$ ($\Omega$ — cell resistance)
 $G_{cell} = 1/R_{cell}$ ($\mho$ — cell conductance)
 $K_{cell}$ is the cell constant (cm$^{-1}$)
 $g_w$ = conductivity of water ($\mho$/cm).

From the above equation 9, it is seen that the output $V_o$ is directly proportional to the conductivity of the salt water.

The actual shape, construction and materials used in the conductivity cell 1 shown in FIG. 1 may vary provided that the voltage electrode 3a, 3b in each electrode set 2a, 2b is located in a current free space created by the current electrodes 4a, 5a, -4b, 5b and the electrode sets 2a and 2b are rigidly fixed with respect to one another.

Figure 4A:
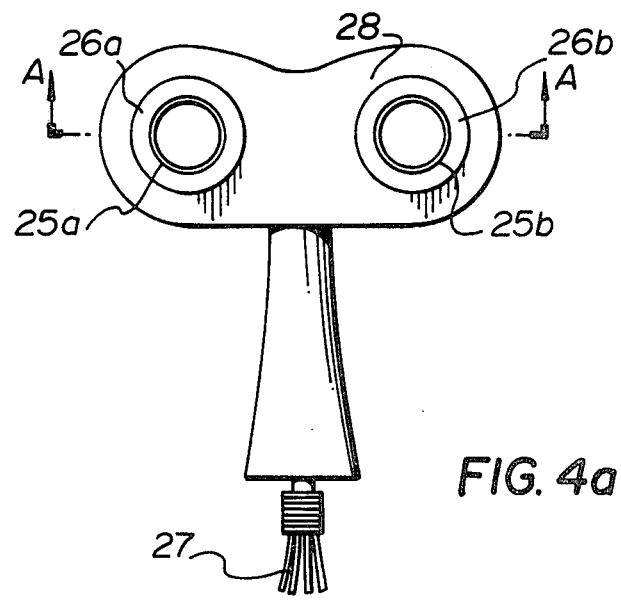
FIGS. 4a and 4b, taken along line A—A, illustrate one embodiment of the conductivity cell in accordance with the present invention.
Figure 4B:
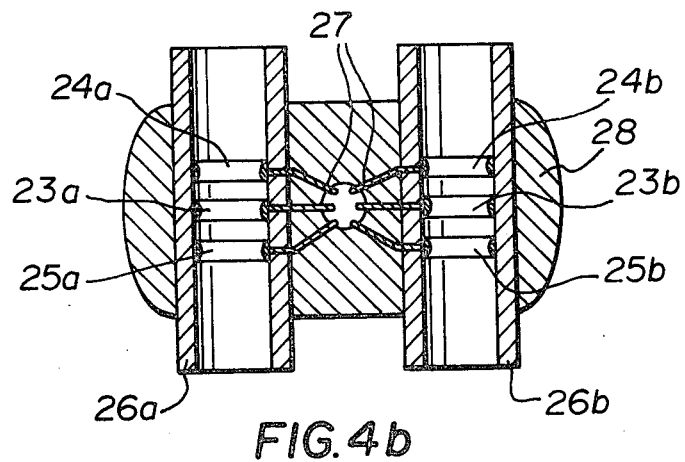

In one embodiment shown in FIGS. 4a and 4b, electrically conductive electrodes 23a, 23b, 24a, 24b, 25a, and 25b are deposited within two supporting tubes 26a and 26b to form electrode sets 22a and 22b. Tubes 26a and 26b may be made of glass or any other non-conducting material. Leads 27 connected to the electrodes are brought through the tube 26a, 26b walls. The sets of electrodes 22a, and 22b, are rigidly positioned with respect to one another by a body 28 of material in which the tubes 26a and 26b are molded or mechanically fixed. The body 28 includes a stem 29 for carrying the leads 27 and for supporting the cell in a chain or other assembly.

Figure 5A:
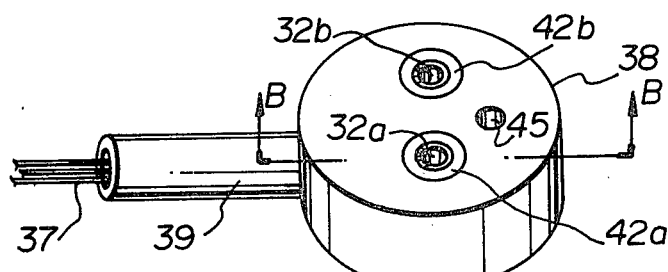
FIGS. 5a and 5b, taken along line B—B, illustrate a second embodiment of the conductivity cell in accordance with the present invention.
Figure 5B:
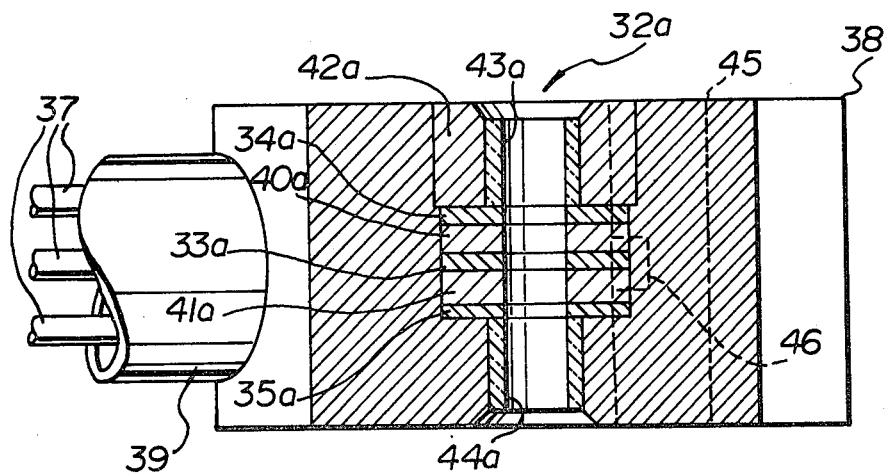

Another embodiment of the cell in illustrated in FIGS. 5a and 5b. The body 38 of the cell is made of non-conductive material such as polyvinyl chloride to which is attached a conduit 39 for carrying the conductors 37 from the cell. Two electrode openings or wells 32a, 32b pass through the body 38 in a spaced relationship at a predetermined distance. The wells 32a and 32b contain three sequential electrodes 34a, 33a, 35a and 34b, 33b, 35b, respectively in the form of conductive washer shaped strips which are spaced a predetermined distance apart by non-conductive spacers 40a–41a and 40b–41b respectively. The electrodes and the spacers are preferably exact fitting and flush on the surface as this provides for the smooth flow of water through the cell and reduces the chances of fouling. The electrodes and spacers are also preferably bonded together in the wells 32a, 32b to prevent the salt water from seeping between them or to the connecting wires. The spacer/electrode assembly in each well 32a, 32b is compressed into place by a non-conductive bushing 42a, 42b which may be threaded for added strength. In order to obtain a smooth and continuous surface of the channel through the spacer/electrode assemblies, non-conducting tubes 43a–44a, and 43b–44b are bonded to each end of the wells 32a, 32a respectively, to be coaxial with the electrodes. The tubes may be made of glass and bonded with silica rubber. The two outer electrodes 34a–35a and 34b–35b in wells 32a, 32b are the current electrodes and therefore may be interconnected within each cell body. The cell body 38 may also include a third well 45 in which is located a temperature sensor 46 such as a thermistor. The temperature sensor 46 is connected to a standard detector circuit such as a Wheatstone bridge to provide temperature measurements.

Figure 6A:
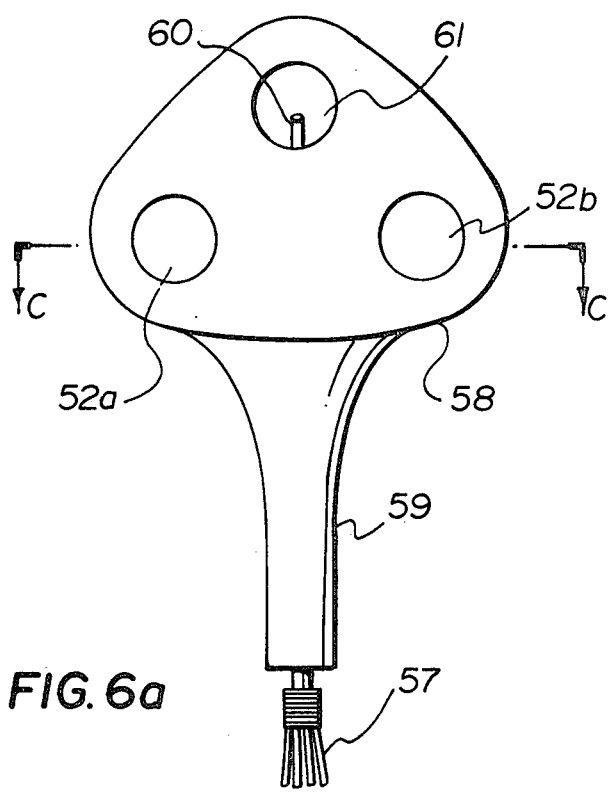
FIGS. 6a and 6b, taken along line C—C, illustrate a further embodiment of the conductivity cell in accordance with the present invention.
Figure 6B:
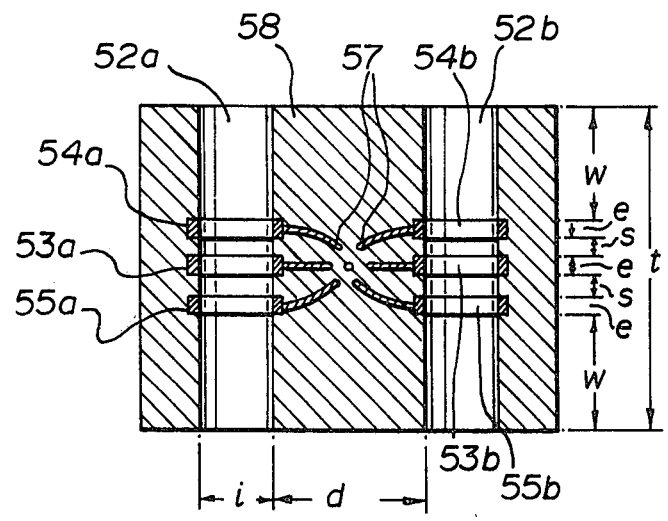

A further embodiment is illustrated in FIGS. 6a and 6b in which the electrodes 54a, 53a, 55a, and 54b, 53b, 55b as well as the conductors or leads 57 are fixed within a unitary molded body 58 so as to be located within electrode wells 52a and 52b. A temperature sensor 60 may also be located within a further well 61. The stem 59 forms a unitary part of the body 58.

Examples of typical dimensions are illustrated in reference to FIG. 6b. The relative spacing of the three electrodes in each well 52a and 52b is not critical as long as the dimensions provide a definite current free space for the voltage electrodes 53a and 53b. An electrode width e in the order of 2 mm is chosen to keep the operational current density low enough to satisfy the external circuit driving capabilities since the value of the polarization impedance "Z" of an electrode is a function of current density at the electrode/water interface. As a practical rule, the electrode spacer width s will be approximately equal to the electrode width e. This will result in an electrode area width of approximately 10 mm and will thus lead to a cell with small physical dimensions. The length w of the wells 52a and 52b from the outer electrode to the outer surface of the cell can be approximately equal to the electrode area width, that is in the order of 10 mm to give an overall well length t of approximately 30 mm. Finally, the inside diameter i of the electrodes and therefore the wells 52a and 52b is in the order of 6 mm. The two separate wells 52a and 52b can be as close to one another as construction methods allow and they need not be parallel and/or in the same plane. However, symmetry is preferred and with the wells approximately parallel and in the same plane, the external current paths are limited to relative short distances outside the cell, minimizing the proximity effects on the cell constant $K_{cell}$. The distance d between the cell wells 52a and 52b are in the order of 20 to 30 mm.

Such a cell as described above will have a cell resistance $R_{cell}$ of approximately 100 Ω in sea water having a 35% salinity and 15° C. temperature.

In a typical system with the circuit described in FIG. 3, the operational frequency for the system is 250 Hz. Power consumption is approximately 7 milliamps from a 12 volt DC (±6 volt DC nominal) single unregulated source. Readings can be taken after 5 seconds following application of power.

We claim:

1. A conductivity cell comprising:

support means having two separate electrode wells, each well being open at both ends and having electrically non-conductive interior walls; and first, second and third electrodes spaced sequentially within each well, the first and third electrodes in each well being interconnected for connection to a current source whereby current flow between the wells produces a detectable potential between the second electrodes.

2. A conductivity cell as claimed in claim 1 wherein each well includes a glass tube as the interior wall.

3. A conductivity cell as claimed in claim 2 wherein each of the first, second and third electrodes in each well consists of a deposition of conductive material of predetermined width about the inner circumference of the glass tube.

4. A conductivity cell as claimed in claim 1 wherein each of the first, second and third electrodes in each well consists of washer shaped conductive strips fixed within the electrode well.

5. A conductivity cell as claimed in claim 4 wherein the first, second and third electrodes in each well are spaced by washer shaped non-conductive strips fixed within the electrode well and a glass tubing is fixed within the electrode well between the outer ends of the electrode wells and the first and third electrodes, the non-conductive strips and glass tubings having a radial thickness approximately equal to the thickness of the electrode conductive strips.

6. A conductivity cell as claimed in claim 4 wherein the washer shaped conductive strips are recessed in the walls of the electrode wells such that the surface of the strips are flush with the electrode well surface.

7. A conductivity cell as claimed in claims 1, 4, 5 or 6 wherein the support means is molded as a single electrically non-conductive unit.

8. A conductivity cell as claimed in claims 1, 2, 5 or 6 wherein the two electrode wells are substantially parallel to one another.

9. A conductivity cell as claimed in claim 1 which further includes temperature sensing means fixed to the support means.

* * * * *